United States Patent
Kylström et al.

(10) Patent No.: US 9,903,849 B2
(45) Date of Patent: Feb. 27, 2018

(54) METHOD FOR DETERMINING THE BULK MODULUS OF FUELS

(71) Applicant: SCANIA CV AB, Södertälje (SE)

(72) Inventors: Kim Kylström, Tullinge (SE); Roger Hälleberg, Nacka (SE)

(73) Assignee: SCANIA CV AB (SE)

(*) Notice: Subject to any disclaimer, the term of this patent is extended or adjusted under 35 U.S.C. 154(b) by 138 days.

(21) Appl. No.: 15/034,260

(22) PCT Filed: Nov. 3, 2014

(86) PCT No.: PCT/SE2014/051293
§ 371 (c)(1),
(2) Date: May 4, 2016

(87) PCT Pub. No.: WO2015/069171
PCT Pub. Date: May 14, 2015

(65) Prior Publication Data
US 2016/0320363 A1    Nov. 3, 2016

(30) Foreign Application Priority Data
Nov. 8, 2013 (SE) .................................. 1351320

(51) Int. Cl.
G01N 33/28        (2006.01)
F02D 41/38        (2006.01)
(Continued)

(52) U.S. Cl.
CPC ..... *G01N 33/2817* (2013.01); *F02D 41/3845* (2013.01); *G01N 33/28* (2013.01);
(Continued)

(58) Field of Classification Search
CPC . G01N 33/28; G01N 33/2817; F02D 41/3845
See application file for complete search history.

(56) References Cited

U.S. PATENT DOCUMENTS 4,782,794 A    11/1988  Hsu et al.
6,102,000 A     8/2000  Shindoh et al.
(Continued)

FOREIGN PATENT DOCUMENTS

| EP | 0 860 601 A2 | 8/1998 |
| EP | 1 571 319 A2 | 9/2005 |
| WO | WO 9427041 A1 | 11/1994 |

OTHER PUBLICATIONS

International Search Report dated Mar. 3, 2015 issued in corresponding International patent application No. PCT/SE2014/051293P/1228-538 PTO-1449.

*Primary Examiner* — John Fitzgerald
(74) *Attorney, Agent, or Firm* — Ostrolenk Faber LLP

(57) ABSTRACT

A method for determination of the bulk modulus of fuels in a fuel system of a combustion engine (2) with a common rail injection system (6), with a high pressure volume (16) including the high pressure side of a high pressure pump (9) and a fuel accumulator (8) with injectors (7) for injection of fuel into the cylinders of the combustion engine. The method including: first determining the volume of the high pressure volume by supplying a fuel with a known bulk modulus to the fuel system and by controlling the high pressure pump (9) so that it performs a pump stroke with the volume of the high pressure volume closed. The value of the determined volume is later used with another fuel in order to determine the latter fuel's bulk modulus.

8 Claims, 3 Drawing Sheets

(51) Int. Cl.
*F02D 19/06* (2006.01)
*F02D 19/08* (2006.01)
*G01N 7/00* (2006.01)

(52) U.S. Cl.
CPC ........ *F02D 19/0628* (2013.01); *F02D 19/087* (2013.01); *G01N 7/00* (2013.01); *Y02T 10/36* (2013.01)

(56) References Cited

U.S. PATENT DOCUMENTS

| | | | |
|---|---|---|---|
| 6,971,368 B2* | 12/2005 | Uchiyama | F02D 41/221 123/359 |
| 7,007,662 B2* | 3/2006 | Sakai | F02D 41/3094 123/299 |
| 7,650,778 B2* | 1/2010 | Puckett | F02D 41/221 73/114.41 |
| 7,891,340 B2* | 2/2011 | Surnilla | F02D 41/062 123/179.17 |
| 2002/0189589 A1* | 12/2002 | Kato | F02M 21/08 123/458 |
| 2005/0103312 A1* | 5/2005 | Uchiyama | F02D 41/221 123/457 |
| 2005/0193982 A1* | 9/2005 | Sakai | F02D 41/3094 123/431 |
| 2008/0035119 A1 | 2/2008 | Marriott et al. | |
| 2008/0302174 A1* | 12/2008 | Puckett | F02D 41/221 73/114.41 |
| 2009/0276141 A1* | 11/2009 | Surnilla | F02D 41/062 701/103 |
| 2010/0319445 A1* | 12/2010 | Yamada | F02D 41/22 73/114.51 |
| 2011/0100329 A1 | 5/2011 | Li | |
| 2015/0240771 A1* | 8/2015 | Pursifull | F02M 65/002 73/114.41 |
| 2015/0285166 A1* | 10/2015 | Surnilla | F02D 33/003 123/294 |
| 2015/0338329 A1* | 11/2015 | Morris | G01N 7/00 73/37 |
| 2015/0354491 A1* | 12/2015 | Ulrey | F02D 41/123 123/294 |

* cited by examiner

METHOD FOR DETERMINING THE BULK MODULUS OF FUELS

CROSS-REFERENCE TO RELATED APPLICATIONS

The present application is a 35 U.S.C. §§ 371 national phase conversion of PCT/SE2014/051293, filed Nov. 3, 2014, which claims priority of Swedish Patent Application No. 1351320-5, filed Nov. 8, 2013, the contents of which are incorporated by reference herein. The PCT International Application was published in the English language.

FIELD OF THE INVENTION

The present invention pertains to a method for the determination of the bulk modulus of fuels in a fuel system of a combustion engine with a common rail fuel injection system, with a high pressure volume comprising the high pressure side of a high pressure pump, and a fuel accumulator with injectors for injection of fuel into cylinders of the combustion engine.

The invention is not limited to any specific type of combustion engine or fuel, and diesel and ethanol may be mentioned as a couple of non-exhaustive examples of fuel. The invention also pertains to the determination of the bulk modulus of fuels in a fuel system for supply of fuel to combustion engines designed for all types of use, such as in industrial applications, crushing machines and in various types of motor vehicles, e.g. ships and trains, although the invention is particularly applicable to wheeled motor vehicles, especially commercial vehicles such as trucks and buses, and will for this reason sometimes be discussed in this use for purposes of elucidating, but not limiting, the invention.

BACKGROUND TECHNOLOGY

At the operation of a combustion engine whose fuel system may be supplied with fuels of different quality, it is of interest to be able to determine the quality of the fuel which is used in order to e.g. be able to adapt the engine's operation, as well as the intervals for the performance of various service measures, to the quality of the fuel. One measure of the quality of the fuel is its bulk modulus, i.e. how well the fuel compresses. Prior art provides for determining the bulk modulus of fuels by sending waves through the fuel with an ultrasound sensor and measuring the velocity of sound in the fuel. Such an approach for determining the bulk modulus of the fuel suffers, in addition to the considerable cost of such equipment, from the disadvantage that the fuel is partly degraded by the sound waves, which increases the wear of parts of the fuel system and the combustion engine, which come into contact with the fuel.

For this reason, a number of different methods to determine the bulk modulus of fuels without the use of such a sensor have been proposed. Examples of such are described in WO 2009121652, U.S. Pat. No. 8,215,161, U.S. Pat. No. 6,805,105, U.S. Pat. No. 7,523,723 and EP 1030047 B1. These methods are, however, relatively complicated and/or have some other drawbacks in terms of reliability.

SUMMARY OF THE INVENTION

The objective of the present invention is to provide a method of the type defined above, which is improved in at least some respect in relation to prior art methods of this type.

In fuel systems of combustion engines with a common rail fuel injection system, the pressure drop in the high pressure volume is a parameter used for important diagnoses, such as the amount of fuel injected into the engine's cylinders. Here, it is important to be able to measure the pressure drop with high accuracy, which is possible with pressure sensors available in the market. In order to be able to use the measured pressure drop with high accuracy as a result for such use, it is, however, important to have knowledge of the volume of the high pressure volume, which due to tolerances at the manufacture of a fuel system may vary by as much as up to 2.5%.

By supplying a fuel, according to the invention, with a known bulk modulus to the fuel system and carrying out a pump stroke and the measurements specified in steps in 1) below in the detailed description comprised of:

a) supplying a fuel with a known bulk modulus ($B_0$) to the fuel system, b) controlling the high pressure pump to perform a pump stroke to supply a given amount (M) of fuel to the high pressure volume while keeping the injectors closed, c) measuring the fuel pressure in the high pressure volume before ($P_1$) and after ($P_2$) said pump stroke. and as a result determining the fuel pressure increase ($\Delta P$) achieved by the pump stroke, d) measuring the temperature (T) of the fuel, and e) calculating the volume (V) of the high pressure volume, based on the values of the temperature (T), a fuel pressure increase ($\Delta P$), the amount (M) of fuel supplied and the fuel's bulk modulus ($B_0$), and the volume of the high pressure volume may easily be determined with high accuracy. Subsequently, this information may be used to determine the bulk modulus of fuels supplied to the fuel system by carrying out a pump stroke, and the measurements and calculations associated therewith, for this fuel.

This also means that it is no longer important to require narrow tolerances at the manufacture of the components defining the high pressure volume, since the volume of the high pressure volume is still reliably determined through the steps noted above in the method according to the invention. Subsequent control of fuel injection in the engine may be adapted to this, and the bulk modulus in different fuels may be determined with the help thereof.

According to one embodiment of the invention, the steps above are carried out the first time the fuel system of the combustion engine is brought into operation, in order to calculate a value for the volume of the high pressure volume to be used step 2) is a second set of steps in 2) below, comprised of subsequently, with other fuel in the high pressure volume, carrying out the steps b)-d) and then calculating the bulk modulus (B) of the fuel, based on the fuel's temperature (T), the pressure increase ($\Delta P$) and the volume (V) of the high pressure volume calculated in step 1) during the later operation of the combustion engine. Thus, the first set of sets is used to determine a "zero" hours volume of the fuel system's high pressure volume. This may occur in the factory when the equipment, in which the combustion engine and the fuel system are comprised, is completed, e.g. in a factory for the manufacture of motor vehicles, or at the first use of the fuel system in a combustion engine.

According to another embodiment of the invention, the second set of step 2) is carried out in connection with the filling of fuel into a fuel tank in the fuel system. In a fuel system in a combustion engine in a motor vehicle, the second set of step 2) is then carried out when the vehicle is refueled, so that the bulk modulus and therefore the quality of the fuel may be determined, e.g. it may be discovered that the vehicle has been refueled with biodiesel instead of fossil diesel. The operation of not only the engine, but also the vehicle, may then be adjusted according to the fuel which is presently in the fuel system.

According to another embodiment of the invention, the second set of step 2) is carried out each time the fuel tank is filled with fuel. By thus determining the bulk modulus and accordingly the quality of the fuel used by the combustion engine, storage of such data may be used at service of such equipment which is impacted by the quality of the fuel, to determine whether certain measures should be taken at such service. For example, a gasket may need to be replaced because the engine has been driven with a certain type of fuel, which is known to produce more wear and tear of the gasket than driving the engine with other fuels.

According to another embodiment of the invention, the method is carried out in a fuel system in a combustion engine in a motor vehicle. Refueling of the motor vehicle may occur in many different places with varying fuel quality and type, which means that it is especially useful to carry out the method according to the invention in motor vehicles, in order to adapt not only the engine's, but also the entire vehicle's operation and maintenance, to the fuel which is actually used.

The invention also pertains to a computer program, a computer program product with the program, an electronic control device all with the features disclosed herein, and all used for a motor vehicle.

Other advantageous features and advantages with the invention are set out in the description below.

BRIEF DESCRIPTION OF THE DRAWINGS

Below are descriptions of example embodiments of the invention with reference to the enclosed drawings, in which.

DETAILED DESCRIPTION OF EMBODIMENTS ACCORDING TO THE INVENTION

Figure 1:
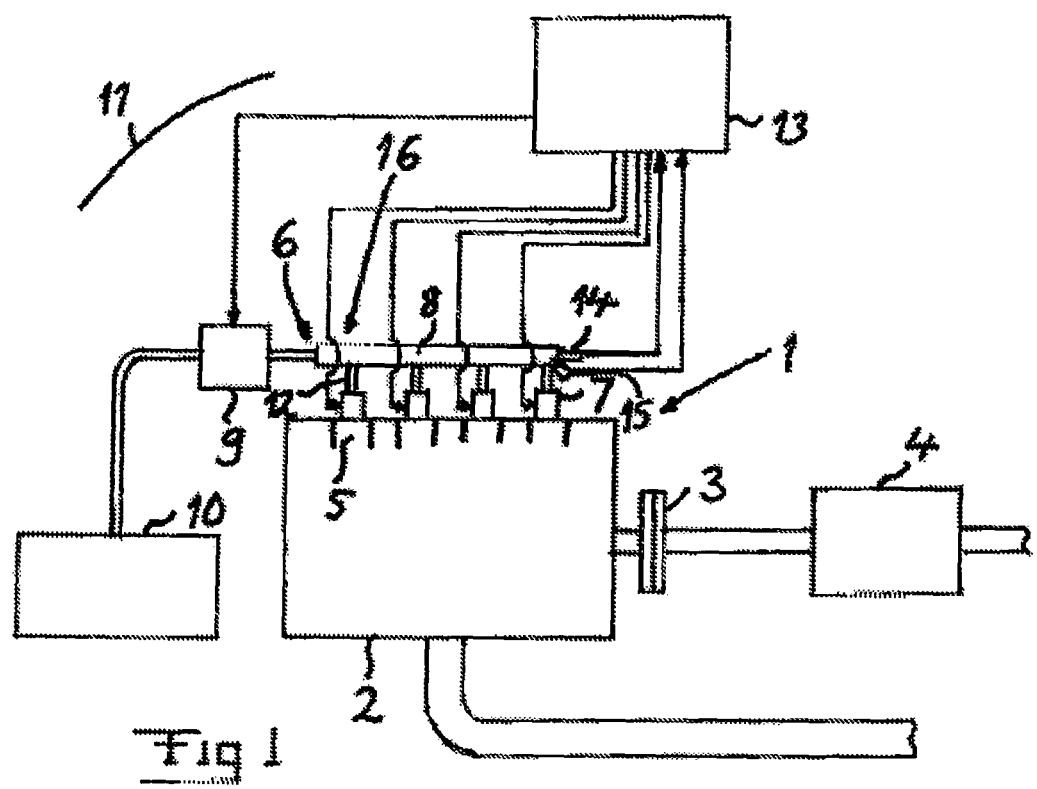
FIG. 1 is a schematic drawing of a combustion engine with a common rail fuel injection system in which a method according to the invention may be applied.

With reference to FIG. 1, a fuel system in a combustion engine, with a common rail injection system to which the method according to the invention is applicable, is described below. A driveline 1 in a motor vehicle comprises a combustion engine 2, e.g. a diesel engine, which is connected to driving wheels (not displayed) of the vehicle via a coupling 3 and a gearbox 4.

The combustion engine 2 comprises several, for example four, schematically indicated cylinders 5. The number of cylinders may naturally be different. Fuel is supplied to the cylinders with the help of a common rail fuel injection system 6, comprising a plurality of electrically controlled injectors 7. Each cylinder of the combustion engine 2 is assigned its own injector. The injectors 7 are connected to a fuel accumulator 8 in the form of a so-called common rail, which includes an accumulator for accumulation of high pressure fuel to be supplied to the injectors. The fuel accumulator 8 is supplied with pressurised fuel by a high pressure pump 9, which receives fuel from a fuel tank 10 of the vehicle 11. The injectors 7 are connected to the fuel accumulator 8 via fuel conduits 12, which branch from the fuel accumulator in order to inject fuel accumulated in the fuel accumulator 8 into the respective cylinders.

An electronic control device 13 is configured for control of the injectors 7 for fuel injection into the respective cylinders. The electronic control device is also adapted to control the high pressure pump 9. A pressure sensor 14 is configured to measure the fuel pressure in the fuel accumulator 8 and send information regarding the measured fuel pressure to the electronic control device 13. Further, a temperature sensor 15 is configured to measure the temperature of the fuel in the fuel accumulator.

A high pressure volume 16 of the fuel system is defined by the volume containing fuel, and lies between the high pressure side of the high pressure pump and the injectors. In order to calculate the volume of this high pressure volume, the electronic control device 13 is configured to control the high pressure pump 9 so that it carries out pump strokes with closed injectors, which means that, via known data of the high pressure pump, the amount of fuel fed into the high pressure volume is thus known. If this has not been done previously, it should be carried out for a fuel with a known bulk modulus $B_0$.

Figure 2:
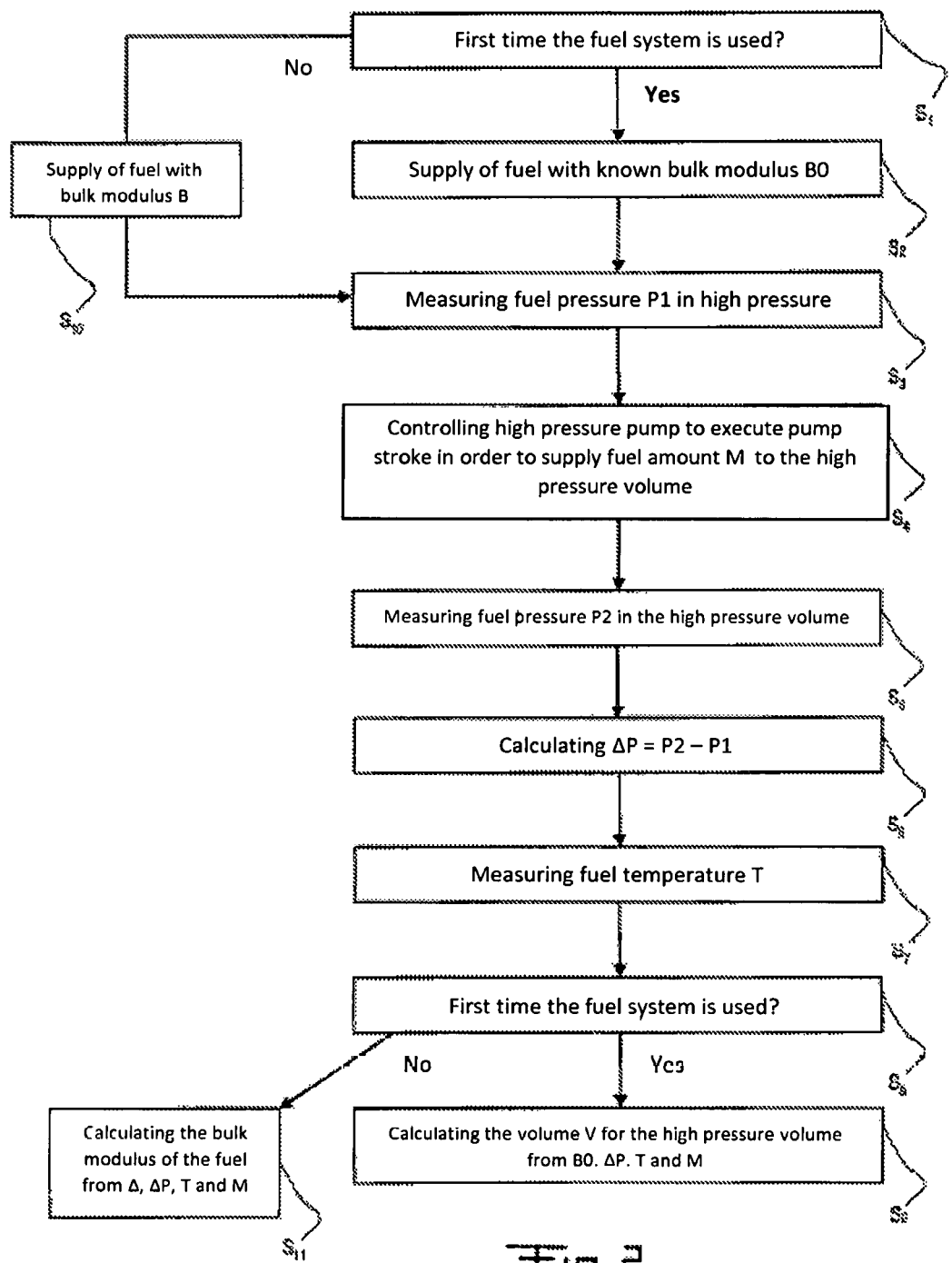
FIG. 2 is a flow chart showing a method according to one embodiment of the invention.

FIG. 2 shows a flow chart illustrating a method according to one embodiment of the invention for determination of the bulk modulus of fuels in a fuel system of the type described above. In a first step $S_1$ the question is asked, if it is the first time the fuel system is taken into operation. If the answer to this question is yes, in a second step $S_2$ a fuel with a known bulk modulus $B_0$ is supplied to the fuel system, whereupon the fuel pressure $P_1$ is measured via the sensor 14 in the high pressure volume. Subsequently, the high pressure pump 9 is controlled so that it carries out a pump stroke to supply the amount M of fuel to the high pressure volume, whereupon the fuel pressure $P_2$ in the high pressure volume is again measured in step $S_5$. Subsequently, the fuel pressure increase $\Delta P$ achieved by the pump stroke is calculated in step $S_6$. Subsequently, or in parallel with or in connection with the previous step, the temperature T of the fuel is measured in step $S_7$. Then the question is asked again, if it is the first time the fuel system is taken into operation. If the answer to this question is yes, in step $S_9$ the volume V of the high pressure volume is calculated based on $B_0$, $\Delta P$, T and M. If, however, the answer to the question is no, the fuel's bulk modulus B is calculated in step $S_{11}$, based on V, $\Delta P$, T and M.

When, subsequently, the fuel system is filled up with new fuel, and the volume V of the high pressure volume is already determined, the answer to the question in step $S_1$ will be no, and fuel with an unknown bulk modulus B will be supplied in order to subsequently have its bulk modulus calculated in step $S_{11}$.

A computer program code for the implementation of a method according to the invention is suitably included in a computer program, loadable into the internal memory of a computer, such as the internal memory of an electronic control device of a combustion engine. Such a computer program is suitably provided via a computer program product comprising a data storage medium readable by an electronic control device, which the data storage medium has the computer program stored thereon. The data storage medium is e.g. an optical data storage medium in the form of a CD-ROM, a DVD, etc., a magnetic data storage medium in the form of a hard disk drive, a diskette, a cassette, etc., or a Flash memory or a ROM, PROM, EPROM or EEPROM type memory.

Figure 3:
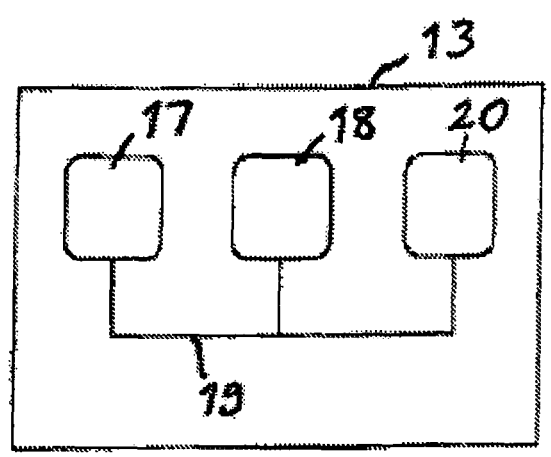
FIG. 3 is a diagram of an electronic control device for the implementation of a method according to the invention.

FIG. 3 illustrates very schematically an electronic control device 13 comprising execution means 17, such as a central processor unit (CPU), for the execution of a computer software. The execution means 17 communicates with a memory 18, e.g. a RAM memory, via a data bus 19. The control device 13 also comprises a data storage medium 20, e.g. in the form of a Flash memory or a ROM, PROM, EPROM or EEPROM type memory. The execution means 17 communicates with the data storage means 20 via the data bus 19. A computer program comprising computer program code for the implementation of a method according to the invention, e.g. in accordance with the embodiment illustrated in FIG. 2, is stored in the data storage medium 20.

The invention is obviously not limited in any way to the embodiments described above, but numerous possible modifications thereof should be obvious to a person skilled in the area, without such person departing from the spirit of the invention as defined by the appended claims.

It is implicit that the high pressure volume must be pressurised before carrying out step b) of the method according to the invention.

The invention claimed is:

1. A method for determining a bulk modulus of fuels in a fuel system of a combustion engine, the engine having cylinders and having a common rail fuel injection system, with a high pressure volume comprising the high pressure side of a high pressure pump and a fuel accumulator with injectors for injecting fuel into the cylinders of the combustion engine or for being closed;
   the method comprising the steps:
   1) determining a volume (V) of the high pressure volume by:
      a) supplying a fuel with a known bulk modulus ($B_0$) to the fuel system;
      b) controlling the high pressure pump to perform a pump stroke to supply a given amount (M) of fuel to the high pressure volume while keeping the injectors closed;
      c) measuring the fuel pressure ($P_1$) in the high pressure volume before and the fuel pressure after said pump stroke ($P_2$), and as a result, determining the fuel pressure increase ($\Delta P$) achieved by the pump stroke;
      d) measuring the temperature (T) of the fuel; and
      e) calculating the volume (V) of the high pressure volume, based on the values of the temperature (T), the fuel pressure increase ($\Delta P$), the amount (M) of fuel supplied and the fuel's bulk modulus ($B_0$); and
   2) subsequently, with other fuel in the high pressure volume, carrying out the steps b)-d) and then calculating the bulk modulus (B) of the fuel, based on the fuel's temperature (T), the pressure increase ($\Delta P$) and the volume (V) of the high pressure volume calculated in step 1).

2. A method according to claim 1, further comprising performing steps 1) a first time the fuel system of the combustion engine starts operation, in order to calculate a value for the volume (V) of the high pressure volume to be used at the performance of step 2) during the subsequent operation of the combustion engine.

3. A method according to claim 1, performed in a fuel system of a combustion engine in a motor vehicle.

4. A method according to claim 1 further comprising performing step 2) in connection with fuel being filled into a fuel tank of the fuel system.

5. A method according to claim 4, further comprising performing step 2) each time fuel has been filled into the fuel tank.

6. A computer program product comprising:
   a data storage medium which is readable by a computer;
   a computer program stored in a non-volatile internal memory of a computer, the computer program comprises a computer program code configured to cause the computer to control the method steps according to claim 1, when the computer program is executed in the computer.

7. An electronic control device configured for determining a bulk modulus of fuels in a fuel system of a combustion engine including a common rail fuel injection system, the device comprising:
   an execution means, a non-volatile memory connected to the execution means and a data storage medium connected to the execution means, the computer program code in the computer program product according to claim 6 being stored on the data storage medium.

8. A motor vehicle comprising the electronic control device according to claim 7, and the vehicle is a wheeled motor vehicle, a truck or a bus.

* * * * *